(12) United States Patent
Winkowski et al.

(10) Patent No.: US 6,432,433 B1
(45) Date of Patent: Aug. 13, 2002

(54) LIQUID BIOCIDAL COMPOSITION OF A FORMALDEHYDE ADDUCT AND AN ISOTHIAZOLONE AND METHOD OF USE

(75) Inventors: Karen Winkowski, Sayreville; Xianbin Liu, Basking Ridge, both of NJ (US)

(73) Assignee: ISP Investments Inc., Wilmington, DE (US)

( * ) Notice: Subject to any disclaimer, the term of this patent is extended or adjusted under 35 U.S.C. 154(b) by 0 days.

(21) Appl. No.: 09/587,532

(22) Filed: Jun. 5, 2000

(51) Int. Cl.[7] .............................................. A01N 25/00
(52) U.S. Cl. ........................ 424/405; 424/405; 514/372
(58) Field of Search ........................... 424/405; 514/372

(56) References Cited

U.S. PATENT DOCUMENTS

| | | | |
|---|---|---|---|
| 3,761,488 A | 9/1973 | Lewis et al. ................. 260/302 |
| 4,252,694 A | 2/1981 | Lewis et al. ................. 252/545 |
| 4,265,899 A | 5/1981 | Lewis et al. ................. 424/270 |
| 4,279,762 A | 7/1981 | Lewis et al. ................. 252/47.5 |
| 4,608,183 A | 8/1986 | Rossmoore ................... 252/36 |
| 4,841,064 A | 6/1989 | Gaglani et al. ............. 548/215 |
| 4,844,891 A | 7/1989 | Rosen et al. ............... 424/76.4 |
| 4,871,754 A | 10/1989 | Bauer et al. ................. 514/373 |
| 4,980,176 A | 12/1990 | Berke et al. ................. 424/682 |
| 5,185,355 A | * 2/1993 | Hsu ........................... 514/372 |
| 5,212,193 A | 5/1993 | Sherba et al. ............... 514/372 |
| 5,294,614 A | 3/1994 | Hsu ........................... 514/244 |
| 5,304,567 A | * 4/1994 | Hsu ........................... 514/372 |
| 5,428,050 A | 6/1995 | Merianos .................... 514/390 |
| 5,620,997 A | 4/1997 | Bolton et al. ............... 514/373 |

FOREIGN PATENT DOCUMENTS

EP 490570 * 6/1992

OTHER PUBLICATIONS

Matsumoto, Shinichi (DN 127:315755, CAPLUS, abstract of JP 09249506 (1997).*
S.P. Denyer, "Mechanisms of Action Biocides", *International Biodeterioration*, 26 89–100 (1990).
Fuller et al., "The Mode of Action of 1,2–benzisothiazolin–3–one on Staphylococcus Aureus", *Letters in Applied Microbiology*, 13–15 (1985).
Pendleton, "U.S. Navy Tracks Performance of EPA–Approved Mildewcides", *Modern Paint and Coatings*, Parts 1 and 2. (1987).
Kull, Eisman, Sylwestrowicz, and Mayer, "Mixtures of Quaternary Ammonium Compounds and Long–Chain Fatty Acids as Antifungal Agents", *Combination Effect of Antifungal Agents*, 1961.

* cited by examiner

*Primary Examiner*—Sabiha Qazi
(74) *Attorney, Agent, or Firm*—Abelman, Frayne & Schwab

(57) ABSTRACT

A synergistic biocidal composition comprising a mixture of a formaldehyde adduct compound and 1,2-benzisothiazolin-3-one.

10 Claims, No Drawings

LIQUID BIOCIDAL COMPOSITION OF A FORMALDEHYDE ADDUCT AND AN ISOTHIAZOLONE AND METHOD OF USE

BACKGROUND OF THE INVENTION

1. Field of the Invention

The present invention relates to a liquid biocidal composition containing (a) formaldehyde adduct compounds and (b) an isothiazolone, which is intended to provide synergistic biocidal. activity against bacteria and fungi. More particularly, the present invention relates to the use of a biocide composition which includes formaldehyde adduct compounds and 1,2- benzisothiazolin-3-one.

2. Description of the Prior Art

Synergistic biological activity exists when the combination of lesser quantities of two biocidal agents results in an equal or greater inhibitory effect than is achieved by the use of either agent acting alone. The synergistic interaction of two or more antimicrobial agents produces an effect that is more than additive in its resultant biological activity.

Formaldehyde adduct compounds are known biocides; their proposed biological target is the cell wall of susceptible microorganisms (S. P. Denyer, 1990. *Mechanisms of action of biocides*. International Biodeterioration, 26:89). Examples of such adduct compounds includeN-methyl-2-hydroxymethyleneoxypropyl-2'-hydroxypropylamineanditsformaldehyde oligomers (manufactured by Creanova Inc., Somerset, N. J. under the trademark NUOSEPT® 145, hereinafter "NMPFA"); oxazolidines such as (4,4-dimethyloxazolidine, manufactured by Creanova Inc. under the trademark NUOSEPT® 101, hereinafter "DMO"), mixtures of bicyclic oxazolidines (such as (5-hydroxymethoxymethyl-1-aza-3,7-dioxabicyclo(3.3.0)octane,5-hydroxymethyl-1-aza-3,7-dioxabicyclo(3.3.0)octane,5-hydroxypoly[methyleneoxy-methyl-1-aza-3,7-dioxabicyclo (3.3.0) octane; manufactured by Creanova Inc. under the trademark NUOSEPT® 95, hereinafter "MBO"; and 2-[(hydroxymethyl) amino]ethanol, (manufactured by Creanova Inc. under the trade mark NUOSEPT® 91, hereinafter "HMAE").

The compound 1,2-benzisothiazolin-3-one (hereinafter "BIT"), an isothiazolone, is an antimicrobial agent. Isothiazolones are disclosed in U.S. Pat. Nos. 3,761,488; 4,105,431; 4,252,694; 4,265,899; 4,279,762; 4,871,754, and 5,620,997. Studies on the microbiological target of BIT suggest that the compound acts on the cytoplasmic membrane thiol-enzymes. (See, e.g., Fuller, S. J., Denyer, S. P., Hugo, W. B., Pemberton, D., Woodcock, P. M. and Buckley, A. J., (1985). The mode of action of 1,2-benzisothiazolin-3-one on Staphylococcus aureus, Letters in Applied Microbiology, 1, 13–15.)

Biocidal combinations with synergistic activities for various microorganisms are known. Different formaldehyde donor compounds have been combined with 3-iodo-2-propynyl butyl carbamate (IPBC), a well known fungicide, to broaden the antimicrobial spectrum of activity. (U.S. Pat. No. 5,428,050; U.S. Pat. No. 4,844,891; D. Pendelton et al. (1987), Modern Paint and Coatings August p:30; September, p:148.) Also, biocidal combinations containing an isothiazolone and other compounds have been disclosed. Some synergistic combinations include isothiazolones and metal complex with functional ligands (U.S. Pat. No. 4,608,183); isothiazolones and hydroxymethylamino acetic acids (U.S. Pat. No. 4,980,176); isothiazolones and substituted anilides (U.S. Pat. No. 5,212,193); and, isothiazolones and triazines (U.S. Pat. No. 5,294,614).

It is an object of the present invention to provide a synergistic biocidal combination, which is more efficacious than known microbicidal compositions.

Another object of the present invention is the provision of a synergistic combination of biocides which is water-soluble and can be uniformly distributed.

Still another object of this invention is the provision of a water-soluble preservative mixture for use in architectural coating applications (i.e. paints, stains) and other coating related materials (adhesives, sealants, joint compounds, latex emulsions, etc), which is effective against a wide range of fungi and bacteria.

SUMMARY OF THE INVENTION

It has been found that the composition of the present invention comprising a mixture of a formaldehyde adduct compound and an isothiazolone exhibits synergistic antimicrobial activity against a wide range of microorganisms; the biological activity of the two compounds acting together being greater than the sum of both compounds acting separately. Synergistic antimicrobial activity may be the result of each biocide having a different mechanism of action on the target microorganisms. The advantages of using a synergistic combination include:

a.) a broadened antimicrobial spectrum of activity;

b.) an increase in effectiveness;

c.) a reduction of the use levels; and d.) a decrease in the toxicity of a given agent to the host and the environment.

The present invention, which combines formaldehyde adduct compounds and 1,2-benziosthiazolin-3-one (BIT), provides a composition having synergistic activity against a wide range of bacteria and fungi.

DETAILED DESCRIPTION OF THE INVENTION

The present invention is directed to a mixture of two biocides designed to control unwanted bacterial and fungal growth in water-based applications, including but not limited to, paints, e.g., acrylics, polyvinyl acetates, styrene-butadienes, etc., coatings, adhesives, sealants, latex emulsions and joint compounds. The liquid biocidal composition of the present invention comprise a mixture of formaldehyde adducts, including NMPFA, DMO, MBO or HMAE, and BIT. The weight ratio of the formaldehyde adduct compound to BIT in the composition of the present invention ranges from about 100:1 to 1:100, more preferably from about 30:1 to 1:30, and most preferably from about 6:1 to 1:6. The BIT can be in the form of an acid or base.

The synergistic antimicrobial activity of the present invention is demonstrated by testing over a range of concentrations and ratios of NMPFA and BIT. The synergistic antimicrobial activity of the present invention is also demonstrated by testing the formaldehyde adduct compounds DMO, MBO or HMAE, and BIT. The examples presented below serve to illustrate the invention and to demonstrate the synergistic results obtained when the two compounds are used in combination, as compared with their effectiveness when used individually.

EXAMPLE I

MIC Data on Microbiological Media

To demonstrate synergism in microbiological growth media a wide range of concentrations and ratios of compounds, generated by serial dilutions were added into Tryptic Soy Agar (TSA) for bacterial evaluations or to Potato Dextrose Agar (PDA) for fungal evaluations. Antimicrobial activity was demonstrated against the bacterium *Bacillus subtilis* (ATCC 27328), *Staphylococcus aureus* (ATCC 6538), *Pseudomonas aeruginosa* (ATCC 10145), *Enterobacter cloacae* (ATCC 13047) and *Escherichia coli* (ATCC 11229), or the fungi *Aureobasidium pullulans* (ATCC 9348), *Gliocladium virens* (ATCC 9645), *Chaetomium globosum* (ATCC 6205), *Aspergillus niger* (ATCC 6275) and *Penicillium funiculosum* (ATCC 11797). The agar was inoculated to contain about $1 \times 10^6$ CFU/ml bacterial cells or fungal spores.

The lowest concentration of each compound or mixture to inhibit visible growth at 32° C. after 48 hours for bacteria and at 28° after 7–10 days for fungi were taken as the Minimal Inhibitory Concentration (MIC). The MIC were taken as end points of activity. End points for the mixture of NMPFA (DMO, MBO or HMAE) and BIT were then compared with the end points for the pure active compound when employed individually.

Synergism was determined by a commonly used method described by Kull, A. C., Eisman, P. C, Sylwestrowicz ,H., D. and Mayer, R. L. (1961). *Applied Microbiology*, 9:538 using the ratio determined by:

$$Q_a/Q_A + Q_b/Q_B = \text{Synergy Index (SI)}$$

where $Q_A$ is the concentration of the formaldehyde adduct in parts per million (ppm), acting alone, which produced an end point. $Q_a$ is the concentration of the formaldehyde adduct in ppm, in the mixture, which produced an end point. $Q_B$ is the concentration of BIT in ppm, acting alone, which produced an end point and $Q_b$ is the concentration of BIT in ppm, in the mixture, which produced an end point.

When the sum of $Q_a/Q_A + Q_b/Q_B$ is greater than one, antagonism is indicated. When the sum is equal to one, additivity is indicated. When the sum is less than one, synergism is demonstrated.

The results, which serve to demonstrate the synergism of these biocidal combinations in microbiological media are compiled in Tables I, Table II and Table III below. Tables I and II demonstrate mixtures of NMPFA (compound A) and BIT (compound B) in various concentrations and ratios acting against bacteria (Table I) or fungi (Table II). Table III demonstrates mixtures of other formaldehyde adducts including DMO, MBO or HMAE (compound A) and BIT (compound B) acting against bacteria and fungi and show:

1. The test organism (bacteria or fungi).
2. The end-point activity in ppm measured by MIC for the compound A alone ($Q_A$), for compound A in the mixture ($Q_a$), for compound B alone ($Q_B$) or for compound B in the mixture ($Q_b$).
3. The weight ratio of compound A to compound B in that particular combination.
4. The calculated synergy index (SI) based on the formula described above.

TABLE I

Formaldehyde adduct (compound A) / BIT (compound B) combination

| Microorganism | A (ppm) | B (ppm) | A:B | Synergy Index |
|---|---|---|---|---|
| *Pseudomonas aeruginosa* | 1,000 | 0 | | |
| | 500.0 | 100.0 | 5:1 | 0.90 |
| | 430.5 | 69.5 | 6:1 | 0.71 |
| | 250.0 | 100.0 | 2.5:1 | 0.65 |
| | 0 | 250.0 | | |
| *Enterobacter cloacae* | 1,000 | 0 | | |
| | 5000. | 100.0 | 5:1 | 0.90 |
| | 495.0 | 4.9 | 100:1 | 0.51 |
| | 493.4 | 6.5 | 75:1 | 0.52 |
| | 490.2 | 9.8 | 50:1 | 0.53 |
| | 483.8 | 16.1 | 30:1 | 0.55 |
| | 430.5 | 69.5 | 6:1 | 0.71 |
| | 25.00 | 100.0 | 2.5:1 | 0.65 |
| | 0 | 2500 | | |
| *Eschenchia coli* | 1,000 | 0 | | |
| | 495.0 | 4.9 | 100:1 | 0.59 |
| | 493.4 | 6.5 | 75:1 | 0.63 |
| | 490.2 | 9.8 | 50:1 | 0.68 |
| | 215.3 | 34.7 | 6:1 | 0.90 |
| | 483.8 | 16.1 | 60:1 | 0.80 |
| | 0 | 50.0 | | |
| *Bacilius subtiis* | 500 | 0 | | |
| | 250 | 10 | 25:1 | 0.90 |
| | 100 | 5.0 | 20:1 | 0.70 |
| | 100 | 10.0 | 10:1 | 0.60 |
| | 99.0 | 1.0 | 100:1 | 0.23 |
| | 98.6 | 1.3 | 75:1 | 0.24 |
| | 98.0 | 2.0 | 50:1 | 0.28 |
| | 96.8 | 3.2 | 30:1 | 0.32 |
| | 50.0 | 10.0 | 5:1 | 0.50 |
| | 43.0 | 6.9 | 6:1 | 0.36 |
| | 0 | 25.0 | | |
| *Staphyiococcus aureus* | 1,000 | 0 | | |
| | 247.5 | 2.5 | 100:1 | 0.30 |
| | 246.7 | 3.3 | 75:1 | 0.31 |
| | 245.1 | 4.9 | 50:1 | 0.34 |
| | 241.9 | 8.1 | 30:1 | 0.40 |
| | 250.0 | 10.0 | 25:1 | 0.45 |
| | 86.1 | 13.8 | 6:1 | 0.36 |
| | 0 | 50 | | |

TABLE II

Formaldehyde adduct (compound A) / BIT (compound B) combination

| Microorganism | A (ppm) | B(ppm) | A:B | Synergy Index |
|---|---|---|---|---|
| *Aspergillus niger* | 1,000 | 0 | | |
| | 430.6 | 69.5 | 6:1 | 0.70 |
| | 483.9 | 16.1 | 30:1 | 0.55 |
| | 490.2 | 9.8 | 50:1 | 0.53 |
| | 495.0 | 4.9 | 100:1 | 0.51 |
| | 1,000 | 2.5 | 400:1 | 1.01 |
| | 1.0 | 100 | 1:100 | 0.40 |
| | 0 | 250 | | |
| *Aureobasidium pulluians* | 500 | 0 | | |
| | 43.0 | 6.9 | 6:1 | 0.22 |
| | 438.9 | 16.1 | 30:1 | 1.29 |
| | 2.1 | 25 | 1:10 | 0.51 |
| | 0 | 50 | | |
| *Gliocladium virens* | >2,000 | 0 | | |
| | 430.6 | 69.4 | 6:1 | 0.91 |
| | 1,500 | 100 | 15:1 | 1.75 |
| | 1.25 | 50.0 | 1:40 | 0.50 |
| | 0 | 100 | | |
| *Chaetomium globosum* | >2,000 | 0 | | |
| | 861.1 | 138.9 | 6:1 | 0.91 |
| | 1,500 | 50 | 30:1 | 0.95 |

TABLE II-continued

Formaldehyde adduct (compound A) / BIT (compound B) combination

| Microorganism | A (ppm) | B(ppm) | A:B | Synergy Index |
|---|---|---|---|---|
|  | 2,000 | 50 | 40:1 | 1.20 |
|  | 1.0 | 100 | 1:100 | 0.40 |
|  | 0 | 250 |  |  |
| Penicillium funiculosum | 250 | 0 |  |  |
|  | 21.5 | 3.5 | 6:1 | 0.23 |
|  | 241.9 | 8.1 | 30:1 | 1.29 |
|  | 0 | 25 |  |  |

TABLE III

Formaldehyde adduct (compound A) / BIT (compound B) combination

| Microorganism | A ppm | B ppm | A:B | Synergy Index |
|---|---|---|---|---|
| Compound A is MBO |  |  |  |  |
| B. subtilis (bacteria) | 125 | 0 |  |  |
|  | 0 | 25 |  |  |
|  | 42.9 | 7.1 | 6:1 | 0.62 |
| G. virens (fungi) | 500 | 0 |  |  |
|  | 0 | 100 |  |  |
|  | 214.3 | 35.7 | 6:1 | 0.79 |
| Compound A is DMO |  |  |  |  |
| B. subtilis (bacteria) | 385 | 0 |  |  |
|  | 0 | 25 |  |  |
|  | 66 | 11 | 6:1 | 0.61 |
| G. virens (fungi) | 770 | 0 |  |  |
|  | 0 | 100 |  |  |
|  | 330 | 55 | 6:1 | 0.98 |
| Compound A is HMAE |  |  |  |  |
| B. subtilis (bacteria) | 250 | 0 |  |  |
|  | 0 | 25 |  |  |
|  | 42.9 | 7.1 | 6:1 | 0.46 |
| G. virens (fungi) | 1,000 | 0 |  |  |
|  | 0 | 100 |  |  |
|  | 214.3 | 35.6 | 6:1 | 0.57 |

EXAMPLE II

The efficacy of each individual compound or their combination was measured in a latex paint artificially contaminated with a mixed inoculum. The microbiological evaluations shown as examples, are based on ASTM D2574–97, "Resistance of emulsion paints in the container to the attack of microorganisms". Briefly, paint samples (e.g. polyvinyl acrylic, PCL 717) were prepared to contain different concentrations of each compound or their mixtures in different concentrations and ratios. Each paint sample thus prepared was then inoculated with a mixed culture of P. aeruginosa, E. cloacae, B. subtilis, B. megaterium and B. licheniformis (final concentration of about $10^6$ CFU/ml) and rechallenged after 7 days (final concentration of about $10^7$ CFU/ml). Paint samples were incubated at 32° C. for the duration of the test and sampled for the presence of viable bacteria on TSA plates. A paint sample was considered appropriately preserved if no bacterial growth was detected after six days in both challenge assays. Table IV shows the synergistic effects of the compounds when tested in a typical polyvinyl acrylic paint. The table summarizes the results obtained when mixtures of NMPFA (compound A) and BIT (compound B) in various concentrations and ratios were added to artificially contaminated paint and show:

1. The end-point activity in ppm obtained when no viable bacteria was detected after both challenges in a paint sample containing the compound A alone ($Q_A$), for compound A in the mixture ($Q_a$), for compound B alone ($Q_B$) or for compound B in the mixture ($Q_b$).
2. The weight ratio of compound A to compound B in that particular combination.
3. The calculated Synergy Index (SI), as described above

TABLE IV

Formaldehyde adduct (compound A) / BIT (compound B) combination

| A (ppm) | B (ppm) | Ratio A:B | SI |
|---|---|---|---|
| 1,000 | 0 |  |  |
| 0 | 170.0 |  |  |
| 430.5 | 69.4 | 6:1 | 0.84 |
| 725.8 | 24.2 | 30:1 | 0.87 |
| 490.2 | 9.8 | 50:1 | 0.55 |
| 246.7 | 3.3 | 75:1 | 0.27 |
| 247.5 | 2.5 | 100:1 | 0.26 |

As can be observed from the data presented in Tables I, II, III and IV, the composition of the invention demonstrated synergistic microbicidal activity. Thus, the combination of these biocides broadens the antimicrobial spectrum of activity when compared with either compound, which when used alone does not achieve optimum results due to weak activity against certain organisms. The increased effectiveness of the combination also provides the benefit of reducing the use levels due to the synergistic effect.

What is claimed is:

1. A biocidal composition to control the growth of microorganisms selected from the group consisting of bacteria and fungi, the composition consisting essentially of a synergistically microbicidally effective mixture of (a) a formaldehyde adduct selected from the group consisting of N-methyl-2-hydroxymethyleneoxypropyl-2'-hydroxypropyl amine, N-methyl-2-hydroxy-oligo-methyleneoxypropyl-2'-hydroxypropylamine, 4,4-dimethyloxazolidine (DMO) and 2-[(hydroxymethyl)amino]ethanol (HMAE); and (b) 1,2 benzisothiazolin-3-one (BIT).

2. A method of controlling the growth of bacteria and fungi in an aqueous-based liquid formulation, consisting essentially of adding to said aqueous formulation a bactericidal and fungicidal effective amount of a synergistic mixture of (a) a formaldehyde adduct selected from the group consisting of N-methyl-2-hydroxymethyleneoxypropyl-2'-hydroxypropyl amine, N-methyl-2-hydroxy-oligo-methyleneoxypropyl-2'-hydroxypropylamine, 4,4-dimethyloxazolidine (DMO) and 2-[(hydroxymethyl)aminojethanol (HMAE); and (b) 1,2 benzisothiazolin-3-one (BIT).

3. The composition of claim 1, wherein the weight ratio of (a) to (b) is from about 100:1 to about 1:100.

4. The composition of claim 3, wherein the weight ratio of (a) to (b) is from about 30:1 to about 1:30.

5. The composition of claim 4, wherein the weight ratio (a) to (b) is from about 6:1 to about 1:6.

6. The method of claim 2, wherein the weight ratio of formaldehyde adduct to BIT is from about 100:1 to about 1:100.

7. The method of claim 6, wherein the weight ratio of formaldehyde adduct to BIT is from about 30:1 to about 1:30.

8. The method of claim 7, wherein the weight ratio of formaldehyde adduct to BIT is from about 6:1 to 1:6.

9. The method of claim 2, wherein the liquid formulation is a water-based paint.

10. The method of claim 9, wherein the water-based paint is selected from the group consisting of styrene-butadiene, polyvinyl acetate and acrylics.

* * * * *